United States Patent [19]
Elkus

[11] Patent Number: 5,462,562
[45] Date of Patent: Oct. 31, 1995

[54] SUTURE PASSER AND METHOD OF USING

[75] Inventor: Robert M. Elkus, West Bloomfield, Mich.

[73] Assignee: Henry Ford Hospital, Detroit, Mich.

[21] Appl. No.: 179,987

[22] Filed: Jan. 11, 1994

Related U.S. Application Data

[63] Continuation-in-part of Ser. No. 63,001, May 17, 1993, abandoned.

[51] Int. Cl.$^6$ ................................................ A61B 17/00
[52] U.S. Cl. ............................ 606/148; 606/139; 289/17
[58] Field of Search ..................................... 606/148, 147, 606/145, 144, 139; 289/17; 604/106, 107

[56] References Cited

U.S. PATENT DOCUMENTS

| | | |
|---|---|---|
| 1,583,271 | 5/1926 | Biro . |
| 1,816,952 | 8/1931 | Bergman . |
| 2,738,790 | 3/1956 | Todt, Sr. et al. ............... 606/145 |
| 2,897,820 | 8/1959 | Tauber . |
| 3,871,379 | 3/1975 | Clarke . |
| 4,172,458 | 10/1979 | Pereyra . |
| 4,935,027 | 6/1990 | Yoon . |
| 5,053,043 | 10/1991 | Gottesman . |
| 5,059,201 | 10/1991 | Asnis . |
| 5,112,344 | 5/1992 | Petros . |
| 5,152,769 | 10/1992 | Baber ............................ 606/145 |
| 5,181,919 | 1/1993 | Bergman . |
| 5,211,650 | 5/1993 | Noda . |
| 5,217,024 | 6/1993 | Dorsey et al. ................. 128/758 |
| 5,250,055 | 10/1993 | Moore et al. .................. 606/148 |
| 5,312,423 | 5/1994 | Rosenbluth et al. ........... 606/139 |
| 5,336,231 | 8/1994 | Adair ............................. 606/148 |

FOREIGN PATENT DOCUMENTS

| | | |
|---|---|---|
| 163715 | 3/1964 | U.S.S.R. . |
| 484865 | 11/1975 | U.S.S.R. . |
| 2157180 | 6/1985 | United Kingdom . |

OTHER PUBLICATIONS

"Endoscopic Suturing and Knot Tying Manual" Ethicon, Inc. (1991).
"Laparoscopic Cholecystectomy: The Methodist Hospital Experience" Richard Graffis (1992).
"Addition of Drugs to Intravenous Fluids" Graham Engle (1971).
"A Universal Ligature Applicator" Lawrence Tinckler (1971).
"A Simple and Rapid Technique for Suture Ligation During Laparoscopic Cholecystectomy" Seigo Kitano (1992).
"The Gazayerli Knotp14 Tying Instrument or Ligator for Use in Diverse Laparoscopic Surgical Procedures" Gazayerli (1991).

*Primary Examiner*—Stephen C. Pellegrino
*Assistant Examiner*—Jeffrey A. Schmidt
*Attorney, Agent, or Firm*—Barnes, Kisselle, Raisch, Choate, Whittemore & Hulbert

[57] ABSTRACT

A suture passer including a stainless steel cylinder that has a rubber gasket at one end adapted to provide a seal through which laparoscopic forceps may be inserted. The suture passer further includes a thin stainless steel guide fastened to the other end of the cylinder and having a laterally extending eye through which a suture may be passed for use.

18 Claims, 4 Drawing Sheets

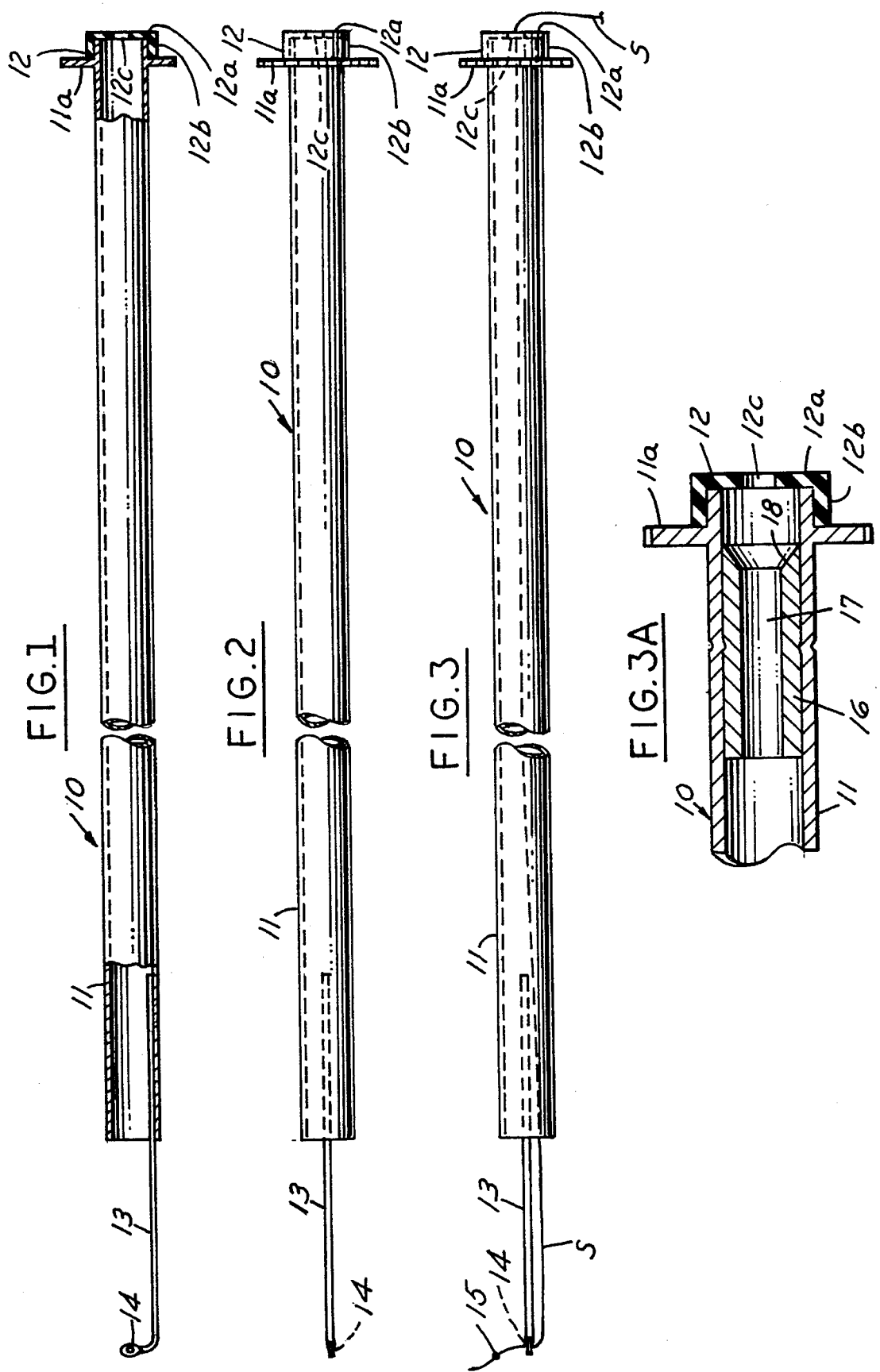

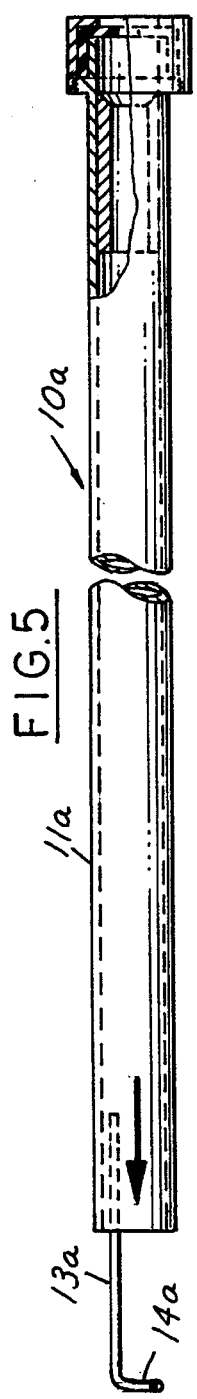
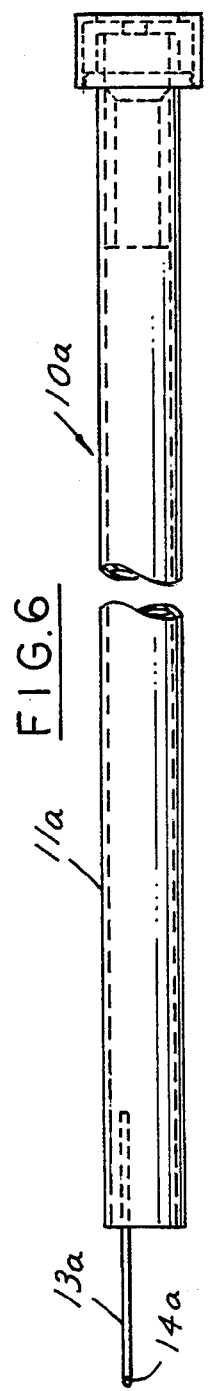
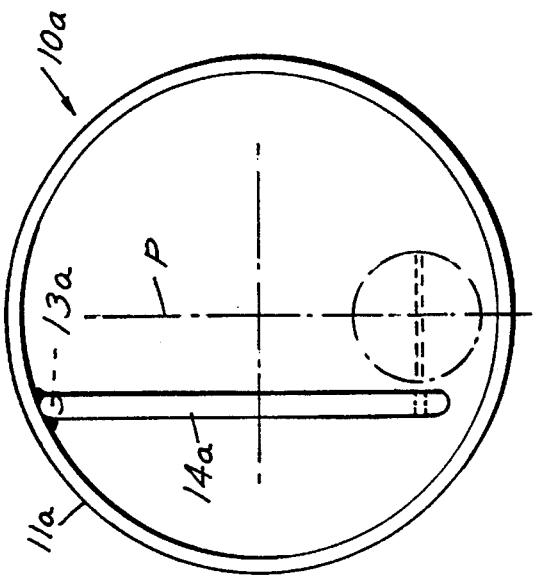
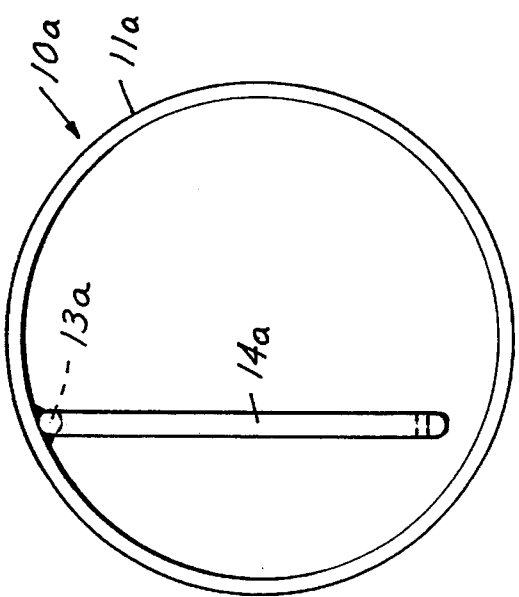

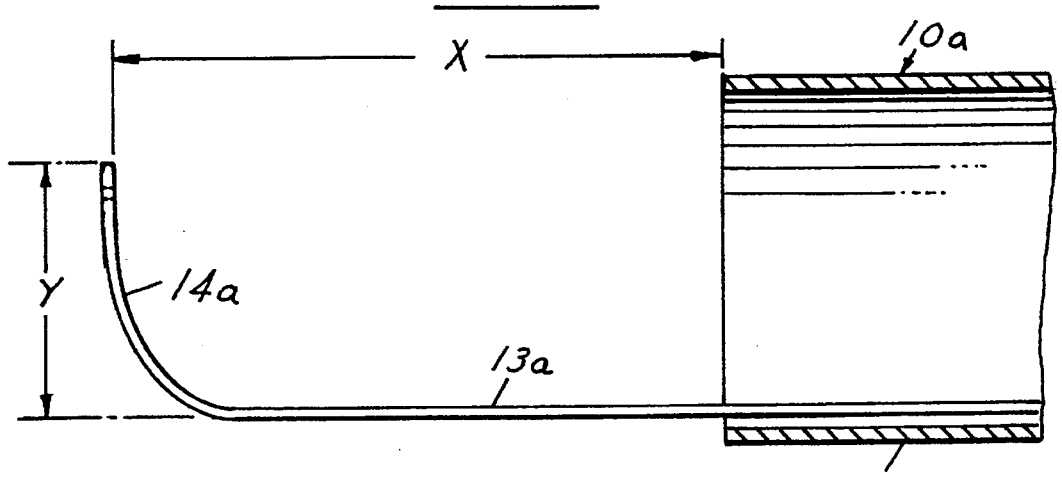
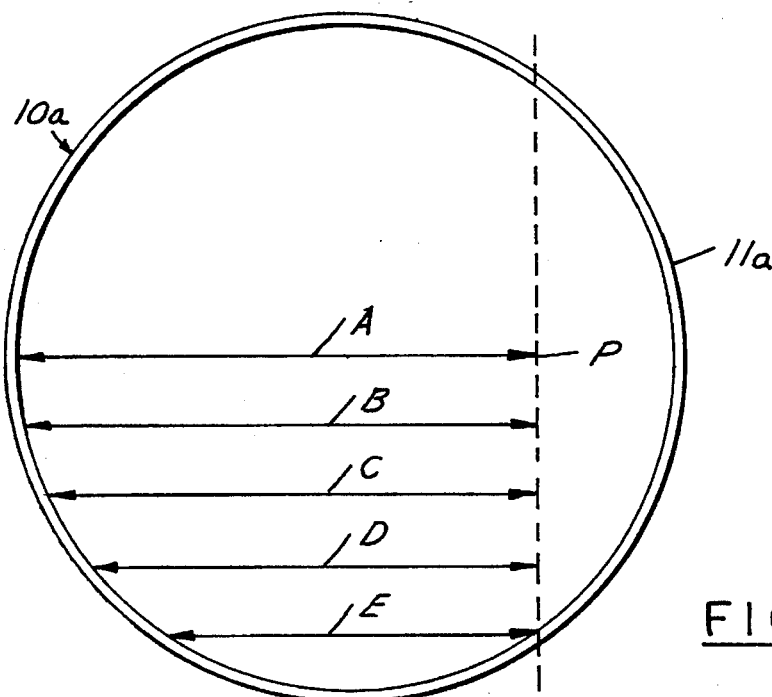
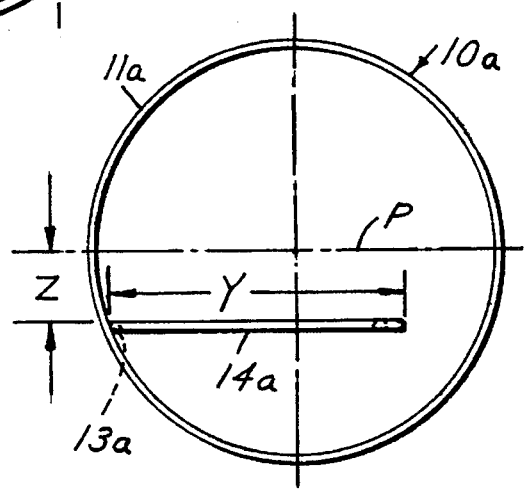

SUTURE PASSER AND METHOD OF USING

This patent application is a continuation-in-part of application Ser. No. 08/063,001 filed May 17, 1993 now abandoned.

This invention relates to a suture passer and a method of using such a passer.

BACKGROUND AND SUMMARY OF THE INVENTION

During laparoscopic surgery, it is frequently necessary to ligate a structure. For example, during laparoscopic cholecystectomy (removal of the gall bladder), the cystic duct (which drains the gall bladder) must be ligated on each side when divided to prevent the leakage of bile.

The description that follows will refer to ligation of the cystic duct as an example. However, this invention can be used to ligate any structure such as an artery, vein, fallopian tube, appendix, etc.

It has been conventional in laparoscopic surgery to utilize a primary cannula for passing of a laparoscope and accessory cannulas for insertion of various instruments.

Among the objectives of the present invention are to provide a novel suture passer which allows the structure requiring ligation to be encircled using only a single cannula. In contrast, existing techniques require two instruments to be inserted through two cannulas to encircle a structure. Once the structure has been encircled by either technique, the suture can be tied with a knot pusher such as a Clarke ligator shown in the U.S. Pat. No. 3,817,379.

In accordance with the invention, a suture passer including a stainless steel cylinder that has a rubber gasket at one end adapted to provide a seal through which laparoscopic forceps may be inserted. The suture passer further includes a thin stainless steel guide fastened to the other end of the cylinder and having a laterally extending eye through which a suture may be passed for use.

DESCRIPTION OF THE DRAWINGS

FIG. 1 is a side elevational view of a suture passer embodying the invention.

FIG. 2 is a top plan view of the suture passer.

FIG. 3 is a view similar to FIG. 2 showing a suture in position.

FIG. 3A is a fragmentary sectional view on an enlarged scale of a portion of the suture passer.

FIG. 5 is a part sectional elevational view of a modified form of suture passer, part being broken away.

FIG. 6 is a tip plan view of the suture passer shown in FIG. 6, part being broken away.

FIG. 7 is an end view on an enlarged scale taken from the left in FIG. 5.

FIG. 8 is a view similar to FIG. 7 showing a forceps diagrammatically.

FIG. 9 is a partly diagrammatic side elevational view.

FIG. 10 is a diagrammatic end view.

FIG. 11 is a partly diagrammatic end view.

DESCRIPTION

Figure 4A:
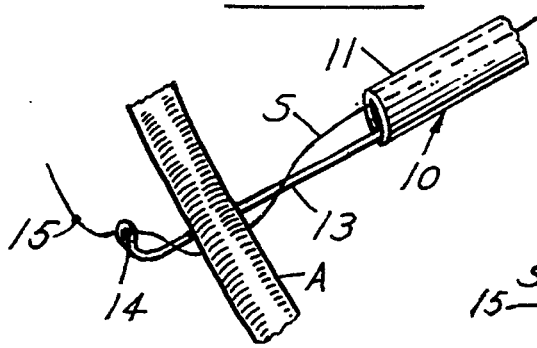
FIGS. 4A–4F are diagrammatic views showing the use of the suture passer.

Referring to FIGS. 1–3, the suture passer 10 embodying the invention comprises a stainless steel cylinder 11 that has a gasket 12 of flexible, resilient material such as rubber at proximal end adapted to provide a seal through which laparoscopic forceps may be inserted. The rubber gasket 12 includes a transverse wall 12a and a peripheral flange 12c engaging the cylinder 11. The transverse wall 12a includes a small opening 12c to allow laparoscopic forceps to be introduced through the cylinder 11 of the suture passer 10. The suture passer 10 further includes a thin stainless steel guide 13 fastened to the distal end of the cylinder and having a laterally extending tip 14 that extends radially inwardly of the cylinder 11. The tip 14 includes an eye that has its axis extending transversely of the tip and axially with respect to the cylinder through which a suture may be passed for use. The tip 14 is connected to the remainder of the guide 13 by an arcuate portion that has a radius extending for 90° so that the axis of the tip 14 and the axis of the guide 13 are tangential to the arcuate portion.

The suture passer also includes a portion 16 on the inner surface of cylinder 11 adjacent the outer end of the cylinder 11 but spaced from the outer end of the cylinder 11. The portion 16 is provided with a central opening 17 and a beveled surface 18 through which an instrument can be inserted and guided. Portion 16 may be separate piece welded or otherwise fixed in cylinder 11.

Prior to insertion, the suture passer 10 is "loaded" by tying a knot 15 in the end of suture S passing through the eye 14. It is then inserted through a previously positioned cannula into the abdomen, and the tip 14 passed around the cystic duct. Laparoscopic forceps F are inserted through the rubber gasket 12 and cylinder 11, and manipulated to grip and pull the suture outwardly from around the cystic duct and out of the abdomen. The suture passer 10 is then withdrawn. The suture has now been passed completely around the cystic duct, and is tied with a knot made outside the abdomen (extracorporeal knot) and pushed into position with a ligator L such as the well known Clarke Ligator® shown and described in U.S. Pat. No. 3,817,379.

The use of the passer in practice is shown more clearly with reference to the sketches FIGS. 4A–4E.

Figure 4B:
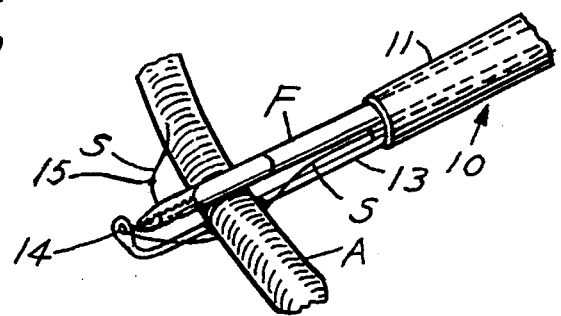
Figure 4C:
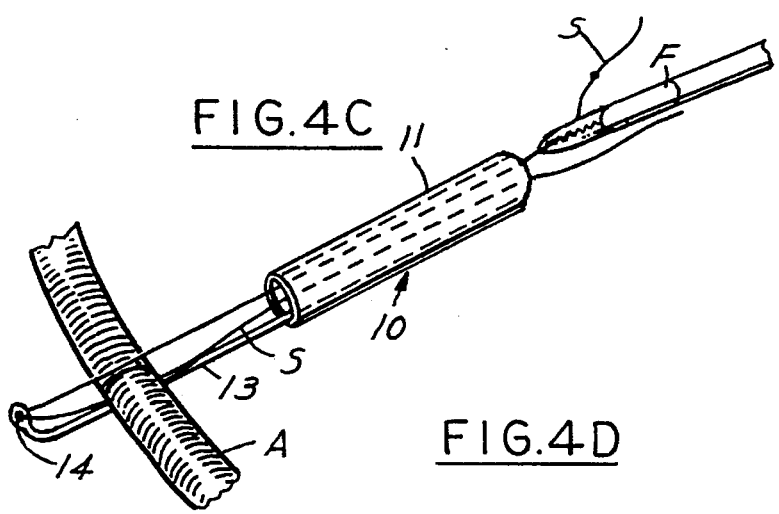
Figure 4D:
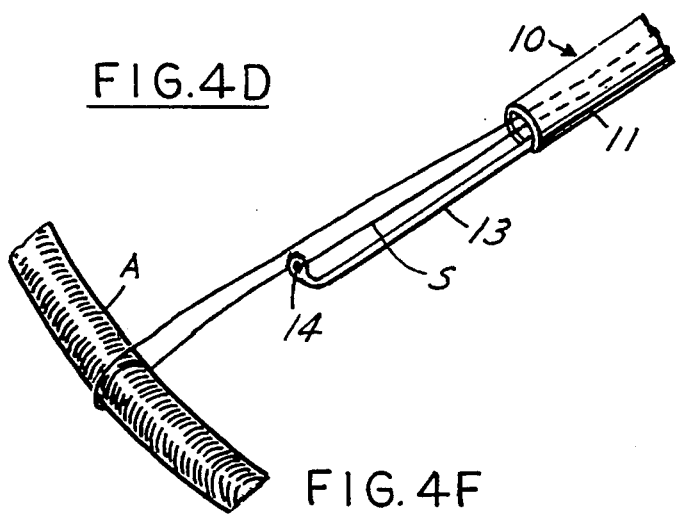
Figure 4E:
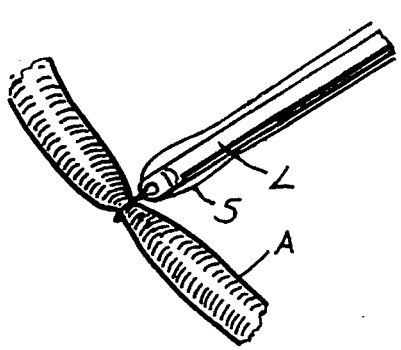
Figure 4F:
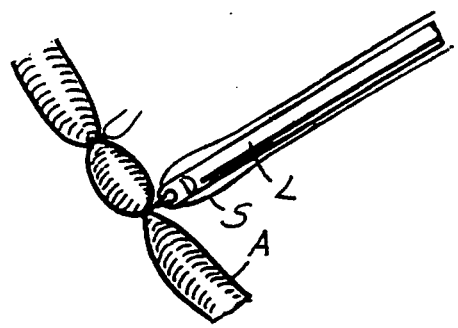

As shown in FIG. 4A, a "loaded" suture passer 10 is inserted into the operating cannula and tip placed around structure to be ligated such a cystic duct A. The laparoscopic forceps F is inserted through suture passer 10 and the suture S is grasped on other side of cystic duct A (FIG. 4B). The forceps are then used to pull one end of suture S out of abdomen. The tip 14 of the suture passer 10 prevents tension on the cystic duct as the suture is pulled out of the abdomen (FIG. 4C). The suture passer S is then withdrawn. The cystic duct A has now been encircled with suture S and is ready to be tied (FIG. 4D). The extracorporeal knot is secured with knot ligator L. As shown in FIG. 4F a second suture has been placed around the cystic duct using the above described technique. The cystic duct A may now be divided.

It can thus be seen that the suture passer in accordance with the invention provides the advantages of using a suture for ligature, but is much easier and faster because only a single cannula is required. The alternate prior art technique of passing a "free suture" around the duct requires two laparoscopic forceps introduced through two cannulas. One instrument must therefore be removed in order to "free up" the second cannula. The prior art Endoloop® and Surgitie® techniques not only require two cannulas, but the cystic duct must be divided before it is ligated. It is preferable to ligate a structure before it is divided, since once traction is lost (after the duct is divided) ligation is much more difficult.

The Endoloop and Surgitie techniques are described in the publication "Endoscopic Suturing and Knot Typing Manual", Ethicon, Inc.® 1991.

The metal clip applicator (Endoclip) is limited by the size of the clip vs. the size of the structure requiring ligation. Additionally, clips may become dislodged when used on an edematous duct (as in acute cholecystitis, when the duct is very swollen). In contrast, a suture is very secure, and may be used to ligate a structure of virtually any size.

In a typical example, the suture passer has a length of about 28 cm; the cylinder has a length 25 cm, an outer diameter of about 10 mm and a thickness of about 0.5 mm. The guide 13 has a diameter of about 1–2 mm. The portion 16 has a length of about 2 cm.

The form of modified suture passer shown in FIGS. 5–8 has been modified to facilitate grasping the end of the suture to tie the suture. The suture passer 10a has the guide 13a positioned such that the tip 14a and guide 13a lie in a longitudinal plane displaced from the center of the cylinder 11a (FIG. 7). As shown in FIG. 5, indicia in the form of an arrow is provided on the cylinder 11a to indicate to the user the proper direction to insert the suture. Since the stainless steel guide is asymmetric with respect to the cylinder, there is a "correct" and "incorrect" direction to insert the suture. This is indicated with an arrow placed on the outside of the guide end of the cylinder. As shown in FIG. 5, an arrow has been placed on the side of the cylinder to indicate to the user the correct side of the eye for the suture to be introduced. The suture is introduced through the eye from the arrow side, such that the knotted end would be facing the forceps, thereby making grasping easier. In all other respects, the suture passer 10a is the same as shown in FIGS. 1–3.

This places the target area for grasping the suture closer to the center of the cylinder. As a result, the positioning of the forceps F for grasping the suture is facilitated (FIG. 8).

As shown diagrammatically in FIG. 11, the line A represents the position of the plane of the the guide 13a and tip 14a. Lines B through E represent possible positions of the plane. The length of the arm 14a must be changed depending on the distance that the plane is displaced from the diametral plane P.

Referring to FIGS. 9 and 10, satisfactory results have been achieved where the suture passer 10a has the following dimensions:

The length X of the guide beyond the cylinder 11a is about 30 mm.

The length Y of the arm 14a is about 8.0 mm.

The distance Z of the plane of guide 13a and arm 14a from the diametral plane P is about 1.5 mm.

The diameter of the cylinder 11a is about 10 mm and the thickness is about 0.3 mm.

It can thus be seen that there has been provided a novel suture passer which allows a structure to be encircled using only a single cannula as contrasted to existing techniques which require two instruments to be inserted through two cannulas to accomplish passing a suture around a structure in preparation for extracorporeal knot ligation.

I claim:

1. A suture passer comprising a cylinder having a proximal end and a distal end and defining a single opening, a gasket of flexible resilient material at said proximal end to provide a seal through which a laparoscopic forceps may be inserted, said opening of said cylinder having a cross-sectional area sufficient to permit passing a laparoscopic forceps, said cylinder including a thin guide fastened in the opening of the cylinder at the distal end of the cylinder, said guide having a lateral arm extending radially inwardly, said guide and said arm lying in a diametral plane of said cylinder, said lateral arm including an eye adjacent said free end through which a suture is passed for use, said free end of said lateral arm of said guide terminating within the projection of said opening.

2. The suture passer set forth in claim 1 wherein the end of said thin guide opposite that having the laterally extending eye extends within the cylinder and is fastened thereto.

3. The suture passer set forth in claim 2 wherein said suture passer including said cylinder and said guide are made of stainless steel.

4. The suture passer set forth in claim 1 wherein said cylinder and said guide are made of stainless steel.

5. The suture passer set forth in claim 1 wherein said cylinder includes an integral flange extending radially outwardly for supporting said gasket.

6. The suture passer set forth in any one of claims 1–5 wherein said guide and said lateral arm lie in a diametral plane of said cylinder.

7. The suture passer set forth in any one of claims 1–5 wherein said guide and said lateral arm lie in a plane displaced radially from a radial plane of said cylinder.

8. The suture passer set forth in claim 7 including indicia on the outside of said cylinder adjacent said guide indicating the direction in which the suture should be inserted to facilitate grasping the suture.

9. The method of ligating a biological structure such as a cystic duct, vein, fallopian tube, appendix or the like which comprises providing a suture passer comprising a stainless steel cylinder having a resilient gasket at one end to provide a seal for introduction of a laparoscopic forceps, inserting a suture passer with the suture in position through a cannula positioned in a small incision in the abdomen, positioning the end of the guide behind and around the structure to be tied, inserting a laparoscopic forceps through the suture passer, grasping the suture with the forceps on the other side of the structure to be tied, pulling the forceps outwardly of the abdomen, withdrawing the suture passer, and tying the suture with a knot ligator, and tying a second suture along the structure to be cut and severing the structure between the two knots thereby formed.

10. A suture passer comprising a cylinder having a proximal end and a distal end and defining a single opening, a gasket of flexible resilient material at said proximal end to provide a seal through which a laparoscopic forceps may be inserted, said opening of said cylinder having a cross-sectional area sufficient to permit passing a laparoscopic forceps, said cylinder including a thin guide fastened to the cylinder at the distal end of the cylinder, said guide having a lateral arm including an eye adjacent said free end through which a suture is passed for use, indicia on the outside of said cylinder adjacent said guide indicating the direction in which the suture should be inserted through the eye to facilitate grasping the suture, said guide and said lateral arm lying in a diametral plane.

11. The suture passer set forth in claim 10 wherein the end of said thin guide opposite that having the laterally extending eye extends within the cylinder and is fastened thereto.

12. The suture passer set forth in claim 10 wherein said suture passer including said cylinder and said guide are made of stainless steel.

13. The suture passer set forth in claim 10 wherein said cylinder and said guide are made of stainless steel.

14. The suture passer set forth in claim 10 wherein said cylinder includes an integral flange extending radially outwardly for supporting said gasket.

15. The suture passer set forth in any one of claims 10–14 wherein said guide and said lateral arm lie in a diametral plane of said cylinder.

16. The suture passer set forth in any one of claims 10–14 wherein said guide and said lateral arm lie in a plane displaced from a radial plane of said cylinder.

17. A suture passer comprising a cylinder having a proximal end and a distal end and defining a single opening, a gasket of flexible resilient material at said proximal end to provide a seal through which a laparoscopic forceps may be inserted, said opening of said cylinder having a cross-sectional area sufficient to permit passing a laparoscopic forceps, said cylinder including a thin guide fastened in the opening of the cylinder at the distal end of the cylinder, said guide having a lateral arm extending radially inwardly, said guide and said arm lying in a diametral plane of said cylinder, said lateral arm including an eye through which a suture is passed for use, said free end of said lateral arm of said guide terminating within the projection of said opening, said guide and said lateral arm lying in a diametral plane displaced from a radial plane of said cylinder.

18. The suture passer set forth in claim 17 including indicia on the outside of said cylinder adjacent said guide indicating the direction in which the suture should be inserted through the eye to facilitate grasping the suture.

* * * * *